(12) United States Patent
Ni et al.

(10) Patent No.: US 10,433,810 B2
(45) Date of Patent: *Oct. 8, 2019

(54) IMAGING SYSTEM CALIBRATION

(71) Applicant: SHANGHAI UNITED IMAGING HEALTHCARE CO., LTD., Shanghai (CN)

(72) Inventors: Cheng Ni, Shanghai (CN); Johannes Stahl, Concord, CA (US); Supratik Bose, Concord, CA (US); Jonathan Maltz, Concord, CA (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 113 days.

This patent is subject to a terminal disclaimer.

(21) Appl. No.: 15/598,331

(22) Filed: May 18, 2017

(65) Prior Publication Data

US 2017/0251995 A1 Sep. 7, 2017

Related U.S. Application Data

(63) Continuation of application No. 14/598,877, filed on Jan. 16, 2015.

(30) Foreign Application Priority Data

Jan. 20, 2014 (CN) .......................... 2014 1 0024798

(51) Int. Cl.
*A61B 6/00* (2006.01)
*G01N 23/046* (2018.01)
*G06T 11/00* (2006.01)

(52) U.S. Cl.
CPC ........... *A61B 6/582* (2013.01); *G01N 23/046* (2013.01); *G06T 11/005* (2013.01); *G01N 2223/303* (2013.01)

(58) Field of Classification Search
None
See application file for complete search history.

(56) References Cited

U.S. PATENT DOCUMENTS 5,442,674 A * 8/1995 Picard .................... A61B 6/583
378/18
5,963,612 A * 10/1999 Navab .................. A61B 6/4441
378/17

(Continued)

FOREIGN PATENT DOCUMENTS

| CN | 101074869 A | 11/2007 |
| CN | 101515370 A | 8/2009 |

(Continued)

OTHER PUBLICATIONS

Baba et al., "Comparison of flat-panel detector and image-intensifier detector for cone-beam CT," Computerized Medical Imaging and Graphics, 26:153-158 (2002).

(Continued)

*Primary Examiner* — Andrew Smyth
(74) *Attorney, Agent, or Firm* — Metis IP LLC

(57) ABSTRACT

A system includes determination of a first sub-matrix of a projection matrix which describes a geometrical relationship between points of a three-dimensional coordinate system of the imaging system and points of a two-dimensional coordinate system of an image detector, determination of a second sub-matrix of the projection matrix, where the first and second sub-matrixes comprise a decomposition of the projection matrix, conversion of a first point of the two-dimensional coordinate system to a first point of the three-dimensional coordinate system based on the first and second sub-matrixes, determination of an updated first sub-matrix of an updated projection matrix, where the updated projection matrix describes a second geometrical relationship between points of the three-dimensional coordinate system (Continued)

and points of the two-dimensional coordinate system, and conversion of a second point of the two-dimensional coordinate system to a second point of the three-dimensional coordinate system based on the updated first and second sub-matrixes.

20 Claims, 8 Drawing Sheets

(56) References Cited

U.S. PATENT DOCUMENTS

| | | | | |
|---|---|---|---|---|
| 5,963,613 | A * | 10/1999 | Navab | A61B 6/4441 378/4 |
| 6,044,132 | A * | 3/2000 | Navab | A61B 6/4441 378/163 |
| 6,049,582 | A * | 4/2000 | Navab | A61B 6/4441 378/17 |
| 6,731,283 | B1 * | 5/2004 | Navab | A61B 6/4441 345/424 |
| 6,753,828 | B2 * | 6/2004 | Tuceryan | G02B 27/017 345/8 |
| 2002/0105484 | A1 * | 8/2002 | Navab | G02B 27/017 345/8 |
| 2002/0113756 | A1 * | 8/2002 | Tuceryan | G02B 27/017 345/8 |
| 2007/0172033 | A1 | 7/2007 | Gorges et al. | |
| 2013/0121457 | A1 * | 5/2013 | Maltz | A61B 6/032 378/4 |
| 2013/0161520 | A1 * | 6/2013 | Jansen | A61B 6/037 250/363.1 |

FOREIGN PATENT DOCUMENTS

| | | |
|---|---|---|
| CN | 101582161 A | 11/2009 |
| CN | 10273184 A | 10/2012 |
| CN | 103006251 A | 4/2013 |

OTHER PUBLICATIONS

Johnston et al., "GPU-based iterative reconstruction with total variation minimization for micro-CT," Proc. SPIE 7622, Medical Imaging 2010: Physics of Medical Imaging, 762238 (Mar. 22, 2010) (11 pages).
Panetta et al., "An optimization-based method for geometrical calibration in cone-beam CT without dedicated phantoms," Physics in Medicine and Biology, 53:3 841-3861 (Jun. 2008).
Selby et al., "Geometry calibration for X-ray equipment in radiation treatment devices," retrieved from https://www.researchgate.net/publication/5271860 on Feb. 22, 2016 (7 pages).
Wein et al., "Self-Calibration of Geometric and Radiometric Parameters for Cone-Beam Computed Tomography," 11th International Meeting on Fully Three-Dimensional Image Reconstruction in Radiology and Nuclear Medicine, Jul. 15, 2011 (Jul. 15, 2011) (4 pages).
Yang et al., "A geometric calibration method for cone beam CT systems," Me. Phys., 33(6): 1695-1706 (Jun. 2006) Author Manuscript.
Hartley and Zisserman, "Camera Models," in Multiple View Geometry in Computer Vision, Chapter 6, pp. 153-165, Cambridge University Press, ISBN: 0521540518 (2004).
M. J. Daly et al.,Geometric calibration of a mobiie C-arm for intraoperative come-beam CT. Medical Physics, 35(5), pp. 2124-2136, 2008.

* cited by examiner

IMAGING SYSTEM CALIBRATION

CROSS REFERENCE TO RELATED APPLICATION

The present application is a continuation of U.S. patent application Ser. No. 14/598,877, filed on Jan. 16, 2015, which claims priority to Chinese Patent Application No. 201410024798.3, filed on Jan. 20, 2014, and entitled "Calibration Method for X-Ray Imaging System." The disclosures of the above-referenced applications are expressly incorporated herein by reference to their entireties.

BACKGROUND

An X-ray imaging system, as shown in FIG. 1, may include an X-ray source 1 and a flat panel detector (FPD) 2 coupled to a gantry 3. Rotation of the gantry 3 causes the X-ray source 1 and the FPD 2 to move in a circular orbit around a patient positioned on a couch 4. The FPD 2 may receive X-rays emitted from the X-ray source 1 after the X-rays have passed through the patient. Because the received X-rays have been attenuated to various degrees by the patient's intervening tissues, the received X-rays may be used to generate a two-dimensional projection image of the tissues.

Two-dimensional projection images may be acquired from different gantry angles, and multiple two-dimensional projection images acquired from different gantry angles may be used collectively to build a three-dimensional reconstructed image of the patient anatomy. Accurate reconstruction of the three-dimensional image requires an accurate expression of a geometric relationship between the three-dimensional volume in which the imaging system resides (e.g., a treatment room) and the two-dimensional images acquired at a given gantry angle and FPD position.

Referring to FIG. 2, the rotation axis of the X-ray source is defined as the International Electrotechnical Commission (IEC) $Y_f$ axis. At the vertical gantry position (known as the zero degree position), the axis which passes through the X-ray source focal spot and which is also perpendicular to the IEC $Y_f$ axis is defined as IEC $Z_f$ axis. The axis perpendicular to the Y-Z plane that passes through the intersection of the $Y_f$ axis and $Z_f$ axis is defined as the IEC $X_f$ axis. In an ideal trajectory, the X-ray source moves in a circular orbit in the vertical X-Z plane, and the center of this circle coincides with the origin $O_f$ of this IEC coordinate system. This point is also known as the machine isocenter. When the gantry is at the zero degree position, the IEC $Z_f$ axis points from the machine isocenter $O_f$ towards the X-ray source and the IEC $X_f$ axis points towards the right while looking towards the gantry. With reference to FIG. 1, calibrated lasers 5 point to the machine isocenter $O_f$ and the crossed lines shown in FIG. 1 indicate axes in different directions.

FIG. 2 further illustrates a two-dimensional pixelized imaging coordinate system defined in the detector plane, defined by the U axis and the V axis. The U axis is the row axis parallel to IEC $X_f$, and the V axis is the column axis anti-parallel to the IEC $Y_f$ axis. The pixel coordinate (u=0, v=0) represents the top left corner pixel of the detector. The ideal detector plane is horizontal (perpendicular to the beam axis) and the planar imaging detector is "centered" by $Z_f$ axis when the gantry is at the zero degree (vertical) position. Moreover, the pixel coordinate of the center of the detector 2 is (W/2$p_u$, H/2$p_v$) where H (respectively $p_v$) and W (respectively $p_u$), respectively represent the width and height of the detector 2 (respectively width and height of each pixel). Also, the IEC coordinate of the point $O_f$ is ideally (0,0-(f-D)), where f and D represent "source to imager distance" (SID) and "source to axis distance" (SAD), respectively.

The actual trajectory of the X-ray source may differ from the above ideal description. For example, the X-ray source may move in and out of the vertical plane by a marginal amount. Moreover, as shown in FIG. 3, the trajectory of the X-ray source might not follow a perfect circle.

The relationship between the X-ray source and the FPD may also vary from the above-described ideal. For example, the relation between the detector assembly and the gantry might not be very rigid. Therefore, at each gantry angle, and due to gravity, the detector assembly may sag a different amount with respect to the central axis (CAX) of the beam (i.e., the line joining the X-ray source and the imaging isocenter), as shown in FIG. 4. In practice, the CAX meets the detector at a pixel location ($u_0$, $v_0$), which is somewhat different from (W/2$p_u$, H/2$p_v$). This point (W/2$p_u$, H/2$p_v$) is known as the principal point or the optical center. Also, as shown in FIG. 4, with respect to the ideal detector, the actual detector may exhibit (a) an out of plane rotation $\eta$ about the axis $u=u_0$ or (b) an out of plane rotation $\sigma$ about the axis $v=v_0$ or (c) a in plane rotation $\phi$ about the point ($u_0$, $v_0$).

However, it has been noted that the out of plane rotations $\eta$ and $\sigma$ are quite difficult to determine with reasonable accuracy and these two angles have only a small influence on the image quality compared to other parameters. In practical implementations, these two angles can be kept small ($\leq 1°$) through good mechanical design and high-accuracy machining. It is therefore reasonable to assume that $\eta=\sigma=0$.

In summary, according to the above model, the plane of the detector is perpendicular to the CAX, but the trajectory of the X-ray source is not a perfect circle and the values of SID f and SAD D in FIG. 2 are not constant for all the gantry angles. Also, the two-dimensional coordinate system comprising the row (U) and column (V) vectors of the image exhibits in-plane rotation and translation about the CAX.

FIG. 5 illustrates these non-idealities. Without loss of generality and applicability to other X-ray imaging systems, the X-ray source of FIG. 5 is a linear accelerator equipped with beam collimation devices, including a multileaf collimator (MLC) that may rotate in a plane that is ideally parallel to that of the corresponding FPD and perpendicular to the CAX. Referring to FIG. 5, the image receptor coordinate axes X_r and Y_r are in the plane of the detector and aligned along X_bld and Y_bld respectively. Due to sag of the detector assembly, the principal point ($u_0$, $v_0$) may differ from the center of the panel. Also, the row (U) and column vectors (V) of the acquired image may exhibit rotation with respect to the projection of the coordinate axis of the MLC (at the zero degree position).

A projection matrix may be used to describe the geometric relationship between any three-dimensional point ($x_f$, $y_f$, $z_f$) in the imaging room and its projection pixel coordinate (u, v) on the two-dimensional FPD. The projection matrix corresponds to a given position of the source/detector (i.e., X-ray source and FPD) pair. For an ideally circular source trajectory, the projection matrix may be written as:

$$\begin{bmatrix} \lambda u \\ \lambda v \\ \lambda \end{bmatrix} =$$

$$\frac{P_\theta}{\begin{bmatrix} 1/p_w & 0 & u_0 \\ 0 & -1/p_h & v_0 \\ 0 & 0 & 1 \end{bmatrix}_\theta * \begin{bmatrix} \cos\phi & -\sin\phi & 0 \\ \sin\phi & \cos\phi & 0 \\ 0 & 0 & 1 \end{bmatrix}_\theta *} * \begin{bmatrix} x_f \\ y_f \\ z_f \\ 1 \end{bmatrix},$$
$$\begin{bmatrix} -f & 0 & 0 & 0 \\ 0 & -f & 0 & 0 \\ 0 & 0 & 0 & 1 \end{bmatrix}_\theta * \begin{bmatrix} 1 & 0 & 0 & 0 \\ 0 & 1 & 0 & 0 \\ 0 & 0 & 1 & -D \\ 0 & 0 & 0 & 1 \end{bmatrix} * \begin{bmatrix} \cos\theta & 0 & -\sin\theta & 0 \\ 0 & 1 & 0 & 0 \\ \sin\theta & 0 & \cos\theta & 0 \\ 0 & 0 & 0 & 1 \end{bmatrix}$$

where the symbol "*" denotes multiplication throughout this document.

However, as noted, the source trajectory is typically not a perfect circle of radius D in the vertical $X_f Z_f$ plane. $[T]_\theta$ and $[R]_\theta$ are the unknown translation and rotation, respectively, from the frame of reference of the aging/treat ent room to the frame of reference of the FPD. The subscript $\theta$ indicates that these transformations change with the gantry angle $\theta$. Therefore, the projection matrix $P_\theta$ for a non-ideal source trajectory may be written as:

$$\begin{bmatrix} \lambda u \\ \lambda v \\ \lambda \end{bmatrix} = \frac{\begin{bmatrix} 1/p_w & 0 & u_0 \\ 0 & -1/p_h & v_0 \\ 0 & 0 & 1 \end{bmatrix}_\theta * \begin{bmatrix} \cos\phi & -\sin\phi & 0 \\ \sin\phi & \cos\phi & 0 \\ 0 & 0 & 1 \end{bmatrix}_\theta *}{\begin{bmatrix} -f & 0 & 0 & 0 \\ 0 & -f & 0 & 0 \\ 0 & 0 & 0 & 1 \end{bmatrix}_\theta * [T]_\theta * [R]_\theta} * \begin{bmatrix} x_f \\ y_f \\ z_f \\ 1 \end{bmatrix}$$

Calibration of an imaging system may include determination of the above projection matrix $P_\theta$ for the non-ideal source trajectory. Conventionally, this calibration involves imaging of a geometry calibration phantom. Geometry calibration phantoms typically consist of radio-opaque beads at known three-dimensional locations with respect to some known frame of reference. This reference frame may be within the phantom itself. The elements of the projection matrix are found by solving equations which relate the known three-dimensional locations within the phantom with the detected two-dimensional pixel locations in a projection image.

Others calibration methods that do not involve a phantom. For example, calibration may include an iterative reconstruction method of perturbing a model projection matrix and generating forward projections to best-match observed projections. Another method uses redundant projections over 180° and optimization to determine misalignment parameters with respect to an ideal projection matrix.

The existing methods for determining a non-ideal projection matrix are inefficient, time-consuming, based on inaccurate assumptions, and/or incompatible with treatment workflow.

DETAILED DESCRIPTION

Figure 1:
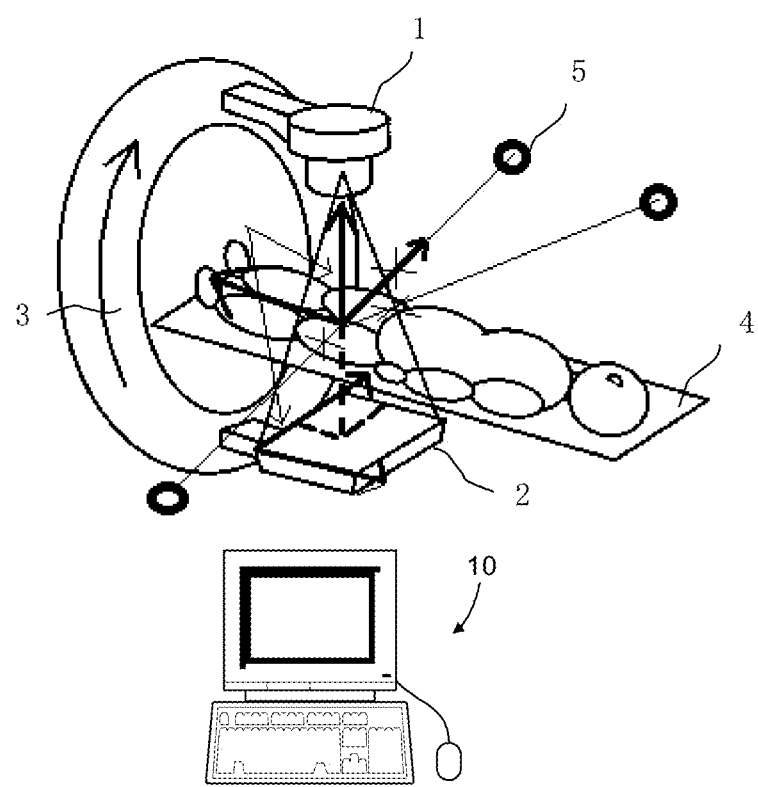
FIG. 1 is a view of an X-ray imaging system.
Figure 2:
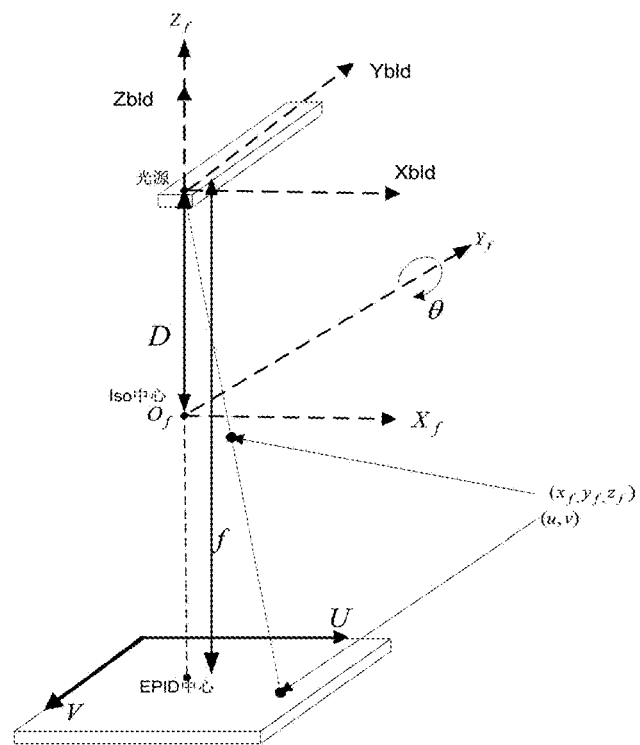
FIG. 2 illustrates a coordinate system associated with an imaging system.
Figure 3:
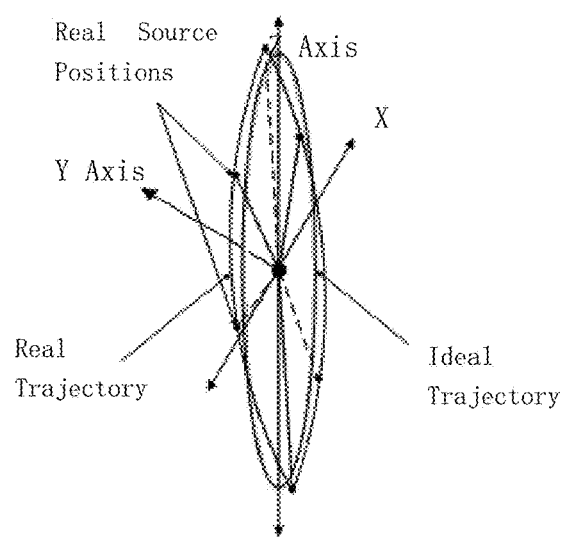
FIG. 3 illustrates trajectories of an X-ray source.
Figure 4:
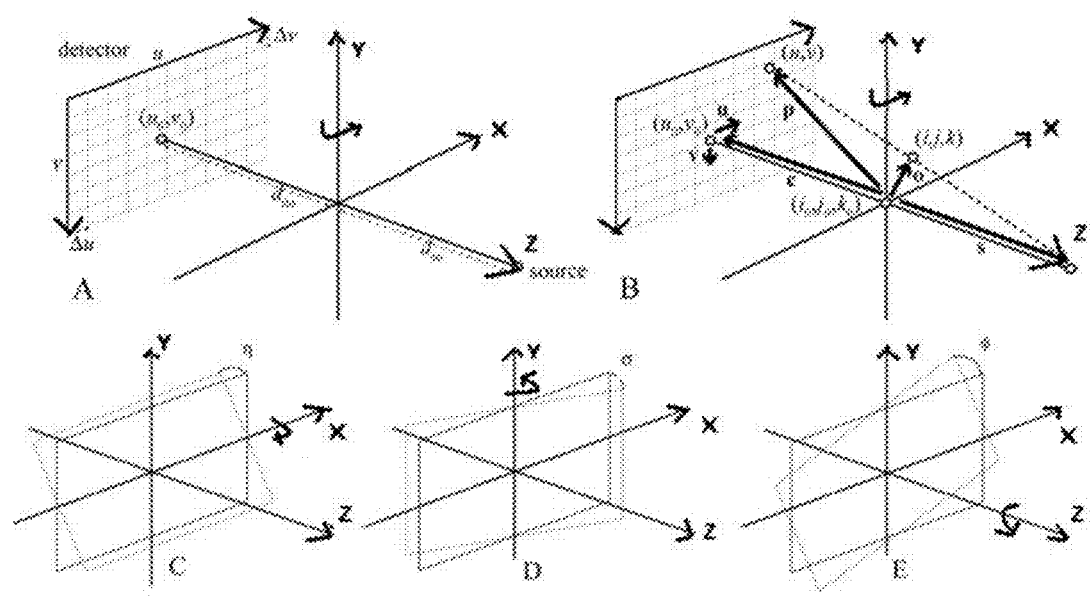
FIG. 4 illustrates rotation of a flat panel detector about different axes.
Figure 5:
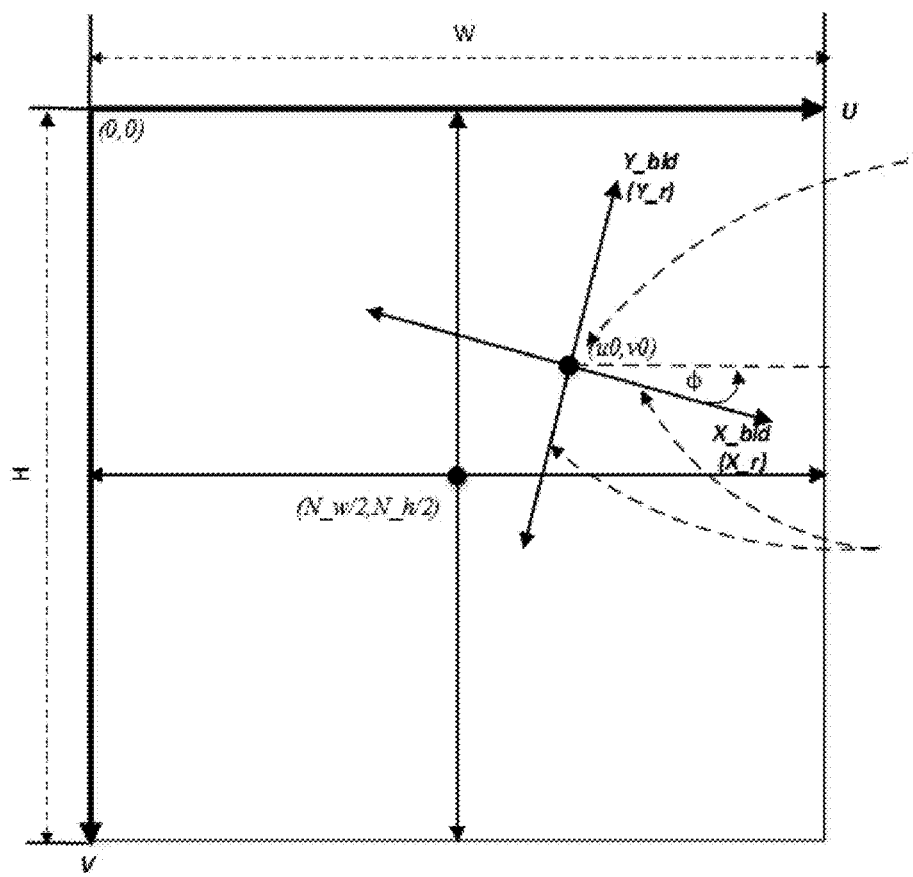
FIG. 5 schematically illustrates the row (U) and column vectors (V) of the acquired image with respect to projection of the coordinate axis of the MLC.

The present inventors have recognized that, for many imaging systems, the assembly which mounts the imaging source 1 to the gantry 3 is often quite rigid, and particularly in a case where the X-ray imaging source 1 is a radiation therapy delivery system (i.e., a linac). As a result, even though the trajectory of the X-ray source 1 does not circumscribe a perfect circle, the actual trajectory may be quite stable and reproducible over a substantial time frame (e.g., several months or years). Moreover, the inventors have recognized that the geometric relationship between the gantry and the detector panel is typically not as rigid (e.g., in order to reduce bulk and/or costs) and therefore varies to a greater extent over time.

The inventors have further discovered a system to decompose the non-ideal projection matrix $P_\theta$ into a "flexible" projection sub-matrix and a "rigid" projection sub-matrix. The terms "flexible" and "rigid" are used for convenience and are not intended to denote any particular degree of rigidity or flexibility. Decomposition of the projection matrix $P_\theta$ into a first projection $P_\theta^{Flexible}$ and a second projection sub-matrix $P_\theta^{Rigid}$ according to some embodiments may be illustrated mathematically as shown below:

$$\begin{bmatrix} \lambda u \\ \lambda v \\ \lambda \end{bmatrix} = \frac{\overbrace{\begin{bmatrix} 1/p_w & 0 & u_0 \\ 0 & -1/p_h & v_0 \\ 0 & 0 & 1 \end{bmatrix}_\theta * \begin{bmatrix} \cos\phi & -\sin\phi & 0 \\ \sin\phi & \cos\phi & 0 \\ 0 & 0 & 1 \end{bmatrix}_\theta}^{P_\theta^{Flexible}} *}{\underbrace{\begin{bmatrix} -f & 0 & 0 & 0 \\ 0 & -f & 0 & 0 \\ 0 & 0 & 0 & 1 \end{bmatrix}_\theta * [T]_\theta * [R]_\theta}_{P_\theta^{Rigid}}} * \begin{bmatrix} x_f \\ y_f \\ z_f \\ 1 \end{bmatrix}$$

According to the embodiments described below, the flexible projection sub-matrix $P_\theta^{Flexible}$ and the rigid projection sub-matrix $P_\theta^{Rigid}$ are determined, and then used to convert coordinates of a two-dimensional coordinate system of a detector to a three-dimensional coordinate system, using calibrated projection matrix $P_\theta = P_\theta^{Flexible} * P_\theta^{Rigid}$. Thereafter, the flexible projection sub-matrix $P_\theta^{Flexible}$ is periodically re-determined according to a first calibration schedule, and the rigid projection sub-matrix $P_\theta^{Rigid}$ is periodically re-determined according to a second calibration schedule, which is less frequent than first calibration schedule.

Calibration of the flexible projection sub-matrix $P_\theta^{Flexible}$ may be faster and less-intrusive than conventional calibration of the non-ideal projection matrix $P_\theta$. According to some embodiments, the flexible projection sub-matrix $P_\theta^{Flexible}$ is re-determined (i.e., calibrated) daily or weekly, and the rigid projection sub-matrix $P_\theta^{Rigid}$ is calibrated every 6-12 months during scheduled maintenance service. The foregoing may result in increased uptime and cost savings.

According to some embodiments, calibration of the flexible projection sub-matrix $P_\theta^{Flexible}$ does not require a phantom, thereby providing further cost savings. As such, calibration of the flexible projection sub-matrix $P_\theta^{Flexible}$ may occur on-the-fly and, if desired, during all scans.

Figure 6:
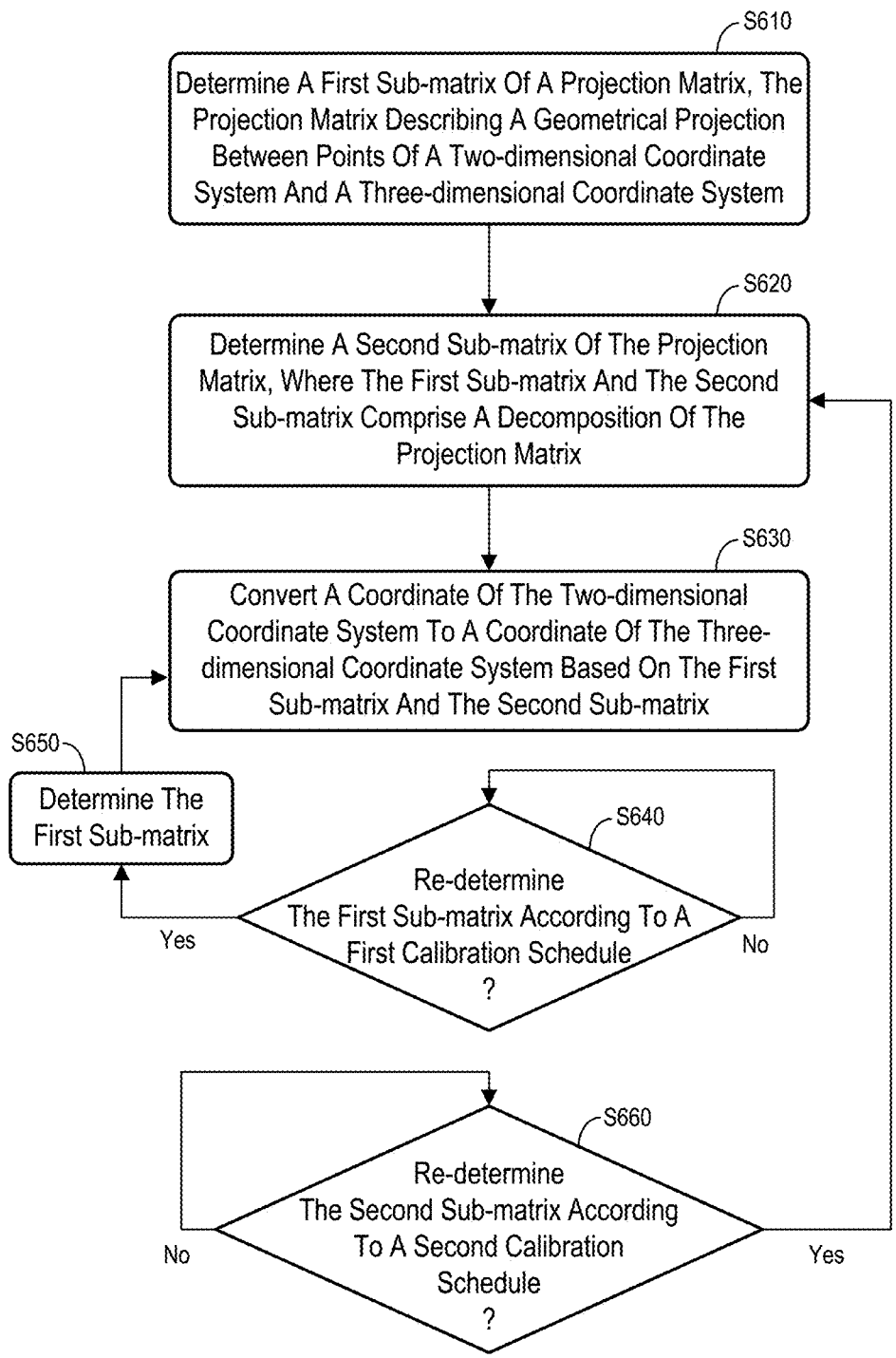
FIG. 6 is a flow diagram of a calibration method for an imaging system according to some embodiments.

FIG. 6 is a flow diagram of process 600 for an imaging system according to some embodiments. Process 600 and the other processes described herein may be performed using any suitable combination of hardware, software or manual means. Software embodying these processes may be stored by any non-transitory tangible medium, including a fixed disk, a floppy disk, a CD, a DVD, a Flash drive, or a magnetic tape.

According to some embodiments, most or all of the steps of process 600 are embodied within executable code of a system control program stored in and executed by one or more processing units (e.g., microprocessors, microprocessor cores, execution threads) of control system 10 of FIG. 1. Imaging according to some embodiments includes, but is not limited to, X-ray portal imaging, cone beam computed tomography projection imaging and fan beam computed tomography imaging. Embodiments may also implement any type or construction of flat panel detector that is or becomes known.

Initially, at S610, a first sub-matrix of a projection matrix is determined. The projection matrix describes a geometrical relationship between a point of a three-dimensional coordinate system and a point of a two-dimensional coordinate system. For example, the projection matrix may describes the geometrical relationship between a point of a three-dimensional coordinate system of an imaging room and a point of a two-dimensional coordinate system of a flat panel detector located in the imaging room.

The first sub-matrix may be associated with in-plane rotation $\phi$ of the flat panel detector and variation in the principal point $(u_0, v_0)$, as described above. According to some embodiments, the first sub-matrix represents the first projection sub-matrix $P_\theta^{Flexible}$ described above.

In some embodiments of S610, the first projection sub-matrix $P_\theta^{Flexible}$ is determined as:

$$P_\theta^{Flexible} = \underbrace{\begin{bmatrix} 1/p_w & 0 & u_0 \\ 0 & -1/p_h & v_0 \\ 0 & 0 & 1 \end{bmatrix}_\theta * \begin{bmatrix} \cos\phi & -\sin\phi & 0 \\ \sin\phi & \cos\phi & 0 \\ 0 & 0 & 1 \end{bmatrix}_\theta}_{P_\theta^{Flexible}}.$$

Accordingly, determination of the first projection sub-matrix $P_\theta^{Flexible}$ according to some embodiments includes determination of pixel dimensions $p_w$, $p_h$, co-plane rotation $\phi$, and principal point $(u_0, v_0)$. Pixel dimensions $p_w$ and $p_h$ may be directly obtained from the design specification of the flat panel detector, and several embodiments for determining co-plane rotation $\phi$, and principal point $(u_0, v_0)$ be described below.

Some embodiments for determining co-plane rotation $\phi$, and principal point $(u_0, v_0)$ (and, as a result, the first projection sub-matrix $P_\theta^{Flexible}$) may be automated, performed on-the-fly and/or performed without use of a phantom. Advantageously, some on-the-fly calibration procedures may be conducted during acquisition of patient images.

A second sub-matrix of the projection matrix is determined at S620. The first sub-matrix determined at S610 and the second sub-matrix determined at S620 comprise a decomposition of the above-described projection matrix. The second sub-matrix is associated with system translations and rotations other than in-plane rotation $\phi$ of the flat panel detector and variation in the principal point $(u_0, v_0)$.

According to some embodiments, the second sub-matrix comprises the rigid projection sub-matrix $P_\theta^{Rigid}$ described above, and is computed at S620 according to:

$$P_\theta^{Rigid} = \begin{bmatrix} -f & 0 & 0 & 0 \\ 0 & -f & 0 & 0 \\ 0 & 0 & 0 & 1 \end{bmatrix}_\theta * [T]_\theta * [R]_\theta,$$

where $[T]_\theta$ represents translation quantity, $[R]_\theta$ represents rotation quantity, and f represents a source to imager distance (SID).

S620 may comprise determination of the complete non-ideal projection matrix $P_\theta$ using a fiducial phantom or other techniques known in the art, and determination of the second projection sub-matrix $P_\theta^{Rigid}$ based on the projection matrix $P_\theta$ and the first projection sub-matrix $P_\theta^{Flexible}$ is as follows: $P_\theta^{Rigid} = [P_\theta^{Flexible}]^{-1} * P_\theta$. An example of a conventional technique for determining a non-ideal projection matrix $P_\theta$ using a fiducial phantom will be provided below.

Next, at S630, a coordinate of the two-dimensional coordinate system is converted to a coordinate of the three-dimensional coordinate system, based on the first sub-matrix and the second sub-matrix. Since the first sub-matrix and the second sub-matrix comprise a decomposition of the projection matrix between the two coordinate systems, a coordinate of the two-dimensional system (e.g., $(u, v)$) may be converted to a coordinate of the other system (e.g., $(x_f, y_f, z_f)$) using the transformation:

$$\begin{bmatrix} \lambda u \\ \lambda v \\ \lambda \end{bmatrix} = \underbrace{\underbrace{\begin{bmatrix} 1/p_w & 0 & u_0 \\ 0 & -1/p_h & v_0 \\ 0 & 0 & 1 \end{bmatrix}_\theta * \begin{bmatrix} \cos\phi & -\sin\phi & 0 \\ \sin\phi & \cos\phi & 0 \\ 0 & 0 & 1 \end{bmatrix}_\theta}_{P_\theta^{Flexible}} * \underbrace{\begin{bmatrix} -f & 0 & 0 & 0 \\ 0 & -f & 0 & 0 \\ 0 & 0 & 0 & 1 \end{bmatrix}_\theta * [T]_\theta * [R]_\theta}_{P_\theta^{Rigid}}}_{P_\theta} * \begin{bmatrix} x_f \\ y_f \\ z_f \\ 1 \end{bmatrix}$$

Operation at S630 may comprise any one or more uses of the projection matrix consisting of the first sub-matrix and the second sub-matrix. For example, S630 may comprise reconstruction of a three-dimensional image based on two-dimensional projection images acquired by the imaging system at various gantry angles, image-assisted patient positioning procedures, radiation field verification, etc. S630 may span several treatment fractions of one or more patients, and any period of time.

S640 and S660 comprise monitoring agents of process 600. Specifically, execution continues at S630 to convert coordinates as desired until it is determined at S640 that the first sub-matrix is to be re-determined. The determination at S640 is based on a first calibration schedule associated with the first sub-matrix. For example, S640 may comprise determining whether a particular amount of time (e.g., one day) has passed since a last determination of the first sub-matrix. The schedule may be event-based. In one example, the first sub-matrix is to be re-determined prior to imaging each patient. The first calibration schedule may comprise a combination of time- and event-based rules.

Flow proceeds to S650 if it is determined at S640 that the first sub-matrix is to be re-determined. The first sub-matrix is re-determined at S650 as described with respect to S610 and flow returns to S630. Accordingly, subsequent coordinate conversion at S630 uses the newly-determined first sub-matrix and the existing second sub-matrix (i.e., $P_\theta = P_\theta^{Flexible}{}_{new} * P_\theta^{Rigid}{}_{current}$).

Similarly, execution continues at S630 until it is determined at S660 that the second sub-matrix is to be re-determined. The determination at S650 is based on a second calibration schedule associated with the second sub-matrix. The second calibration schedule may be less frequent than the first calibration schedule according to some embodiments. The second calibration schedule may indicate a re-determination of the second sub-matrix every six months, at each service appointment, or any combination thereof.

If it is determined at S660 to re-determine the second sub-matrix, flow returns to S620 to re-determine the second sub-matrix and then proceeds as described above. In this regard, subsequent coordinate conversions at S630 use the currently-existing first sub-matrix and the newly-determined second sub-matrix (i.e., $P_\theta = P_\theta^{Flexible}{}_{current} * P_\theta^{Rigid}{}_{new}$).

Some embodiments for determining the co-plane rotation θ, and the principal point ($u_0$, $v_0$) for determination of the first projection sub-matrix at S610 will now be described in more detail. Some of the described embodiments provide automated phantom-less on-the-fly determination of the first projection sub-matrix.

Initially, a MLC of the imaging device is set to a predefined leaf configuration. The predefined configuration may be symmetric about the Y axis. Next, at a single gantry angle, a first image is acquired by the detector while the collimator is at a 0 degree rotational position and a second image is acquired by the detector while the collimator is at a 90 degree rotational position. The two images are superimposed to obtain a rectangular-shaped MLC pattern.

Figure 7:
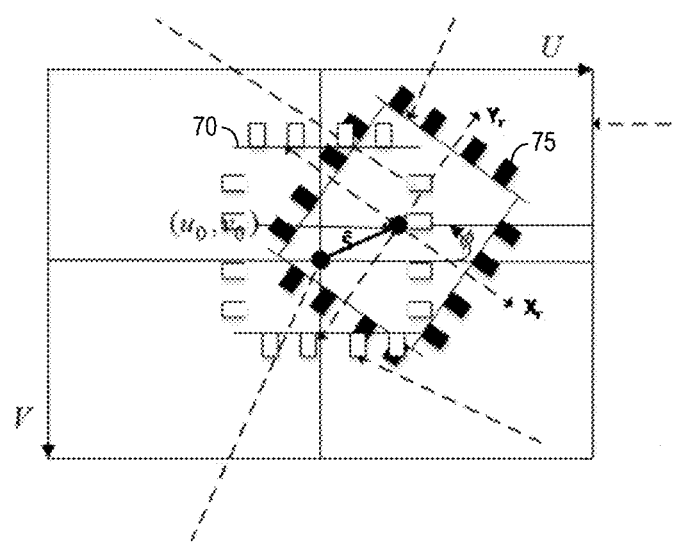
FIG. 7 illustrates determination of a first sub-matrix of a projection matrix using an MIX pattern according to some embodiments.

FIG. 7 illustrates an "ideal" MLC pattern 70 for a given leaf configuration. The ideal pattern 70 represents a scenario in which the detector exhibits no co-plane rotation or translation. The actually-acquired MLC pattern 75 is also shown, which exhibits both co-plane rotation and translation with respect to the ideal pattern 70. The co-plane rotation $\phi$ and the translation vector $\hat{s}$ can be computed by registering the "ideal" MLC pattern 70 with the acquired MLC pattern 75 and then computing the principal point ($u_0$, $v_0$) from the translation vector $\hat{s}$.

Figure 8:
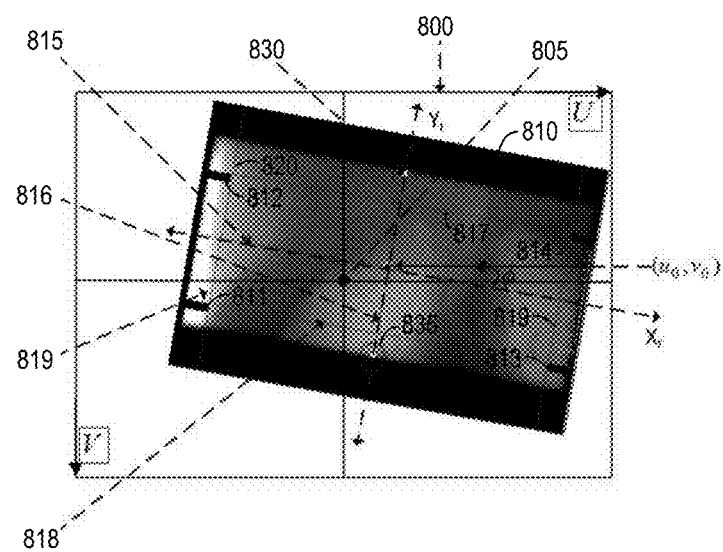
FIG. 8 illustrates determination of a first sub-matrix of a projection matrix using an MLC according to some embodiments.

According to some embodiments, only one projection image is acquired, while the collimator is at 0 degrees, to determine the co-plane rotation $\phi$, the translation vector $\hat{s}$, and the principal point ($u_0$, $v_0$). FIG. 8 illustrates an example of a projection image 810 acquired on detector surface 800, having a imaging center point 805. As shown, the MLC is configured to allow four predetermined leaves 811-814 to enter the image field. The lateral edges of the leaves are parallel to the $X_r$ axis 815 and each lateral edge is at a known distance from the $X_r$ axis. Therefore, even one lateral edge of a leaf in the acquired image can be used to identify the $X_r$ axis. Similarly, the longitudinal end edges of the leaves are parallel to the $Y_r$ axis and each longitudinal edge is at a known distance from the $Y_r$ axis. Therefore, even one longitudinal edge of a leaf can be used to identify $Y_r$ axis.

Figure 9:
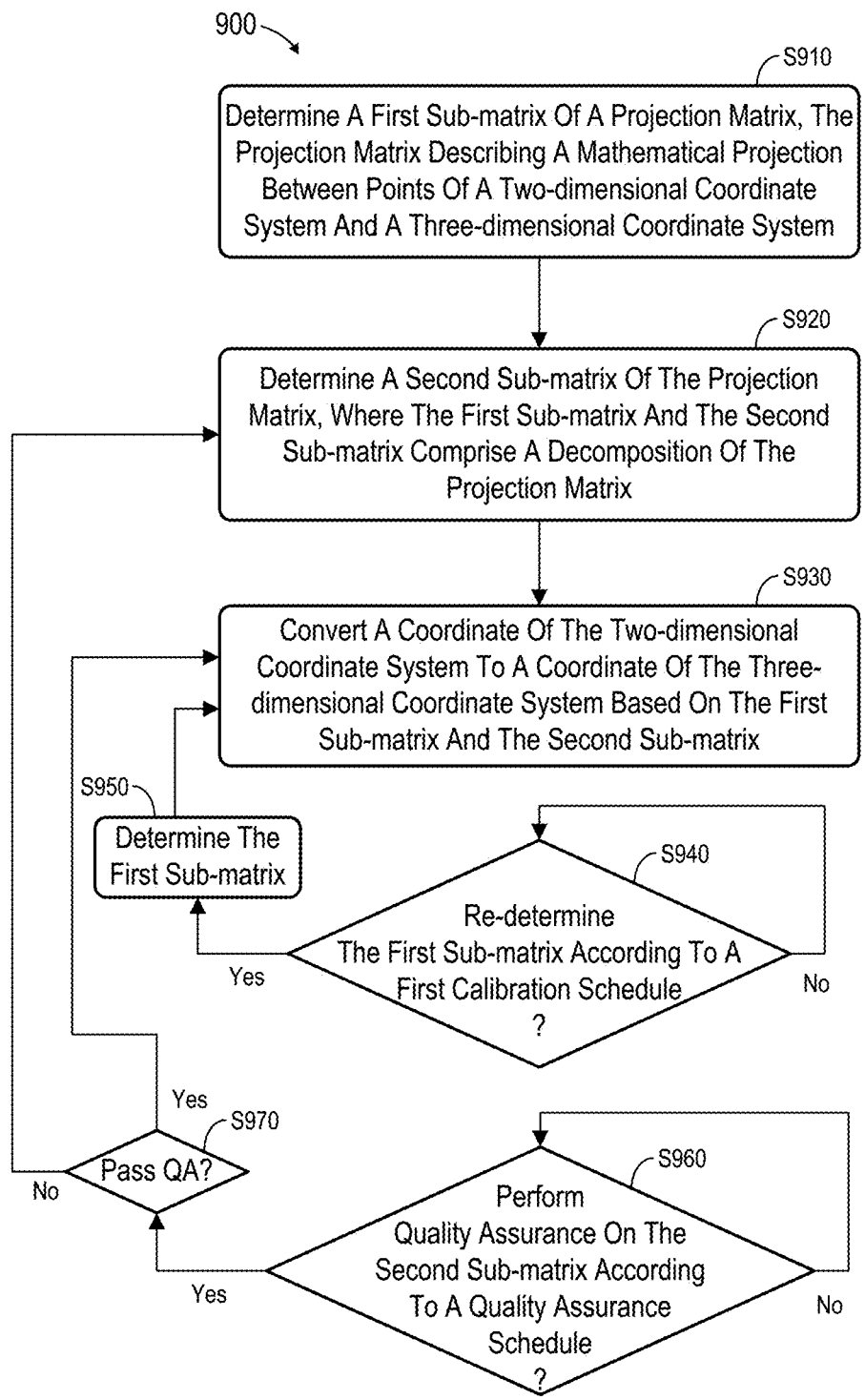
FIG. 9 is a flow diagram of a calibration method for an imaging system according to some embodiments.

According to some embodiments, and also illustrated in FIG. 9, the edges of predetermined leaves are symmetrically placed about the $X_r$ and $Y_r$ axes. Therefore, after identifying the lateral edges and lateral lines defined thereby such as lines 817 and 818, a line symmetrical to the lateral lines may be determined as the $X_r$ axis 815. Similarly, after identifying the longitudinal end edges of equally-extended leaves from opposing banks of leaves and longitudinal lines defined thereby such as lines 819 and 820, a line symmetrical to the longitudinal lines may be determined as the $Y_r$ axis 816.

As described above, the planned and measured positions of the end (longitudinal) edges of the leaves may be used to identify the $Y_r$ axis. However, since the leaves are typically prevented from significantly restricting the open-field, the end positions of these protruded leaves lie near the boundary. While the lateral edges can be detected with better accuracy, the effect of beam penumbra near the boundary may affect the accuracy of detecting the end (i.e., longitudinal) edge of the leaves if those edges are near the boundary. Therefore, in another variation of on-the-fly determination of the first sub-matrix, the MLC may use Y-jaws with a center "notch" such as the notches of FIG. 8. The $Y_r$ axis 816 may then be identified by identifying the notches 830 and 835 in the projection image 810 and joining them with a straight line.

A notch as described above may be simulated by positioning an opposing pair of leaves near the upper Y boundary close together, leaving a narrow opening in the center between the leaves, and similarly positioning an opposing pair of leaves near the lower Y boundary. The $Y_r$ axis may then be identified by identifying the openings in the projection image and joining them with a straight line.

The following is a description of a conventional technique for determining the non-ideal projection matrix $P_\theta$. As described above, the non-ideal projection matrix $P_\theta$ may be used in some embodiments, in conjunction with the first sub-matrix determined at S610, to determine the second sub-matrix at S620.

Initially, a geometry phantom is placed approximately at the imaging isocenter of the imaging system, with the axis of the phantom being approximately aligned with the expected IEC axis. Images of the phantom are acquired at each of many gantry angles (e.g., at 0.5 or 1 degree intervals). Fiducials are detected in the images and linear equations are formulated which relate three-dimensional locations of the fiducials and the corresponding two-dimensional projections, with the parameters of the projection matrix $P_\theta$ as unknowns.

The overdetermined system of linear equations is solved to obtain $P_\theta^{phantom}$ in the phantom coordinate system, and the location of the imaging source is determined in the phantom coordinate system. Next, a circle is fit through the source points, the center of rotation and plane of rotation are determined, and the isocenter is located at the center of rotation. The IEC Y axis is determined to be normal to the plane of rotation and the source location is projected at gantry 0 degree position on the vertical plane. The IEC Z axis is the unit vector from the center to the projected source location and the IEC X axis is the cross product of the Y and Z axis. Using the above information. $P_\theta^{phantom}$ is transformed to the projection matrix $P_\theta$.

FIG. 9 is a flow diagram of process 900 according to some embodiments. Process 900 is similar to process 600, but instead of determining whether or not to re-determine the second sub-matrix according to a second calibration schedule, process 900 includes (at S960) a determination of whether to execute a quality assurance procedure to determine whether the currently-determined second sub-matrix (e.g., $P_\theta^{Rigid}$) is acceptably valid, and (at S970) the quality assurance procedure itself. Accordingly, re-determination of the second sub-matrix may be avoided if the current second sub-matrix is determined to be acceptable at S970.

Avoidance of unnecessary determination of the second sub-matrix may be desirable because this determination (as described above) requires the use of phantoms with embedded fiducials at known three-dimensional locations with respect to a frame of reference. A quality assurance procedure according to some embodiments only requires assurance phantoms at static locations in the imaging room. Moreover, knowledge of the three-dimensional locations of the assurance phantoms is not required. The quality assurance procedure may therefore be performed on-the-fly and with significantly less disruption than re-determination of the second sub-matrix.

A quality assurance procedure according to some embodiments is intended to determine whether the current source trajectory suitably matches the trajectory modeled by the currently-determined second sub-matrix. According to some embodiments, it is first ensured that the first sub-matrix (e.g., $P_\theta^{Flexible}$) current for all gantry angles. Next, spherical radio-opaque beads (e.g., ball bearings) are attached to the couch, projections images of the beads are acquired (with or without a patient positioned on the couch), and a three-dimensional image of the beads is reconstructed from the projection images, using the projection matrix composed of the current first sub-matrix and the current second sub-matrix.

Next, the dimensions and/or blur of the ball bearings are determined in three-dimensional space from the three-dimensional image. If the determined dimensions are within a suitable threshold of the actual dimensions, and/or if the detected blur is not significant blur, it is determined that the current second sub-matrix does not require re-determination. Notably, the foregoing procedure may be performed quickly and/or during patient imaging, and may eliminate unnecessary determination of the second sub-matrix (i.e., $P_\theta^{Rigid}$).

An alternative quality assurance procedure attempts to match computed locations of fiducials from different pairs of gantry angles. After ensuring that the first sub-matrix (e.g., $P_\theta^{Flexible}$) is current for all gantry angles, two-dimensional projections $(u^1, v^1), \ldots, (u^N, v^N)$ of spherical radio-opaque beads are acquired from gantry angles $\theta^1, \ldots, \theta^N$, respectively. The beads are attached to the couch in locations (possibly near the edge of open field) such that their projection is visible even while acquiring portal images or CBCT projection images of the patient.

Assuming the unknown three-dimensional location of such a bead to be $(x_f, y_f, z_f)$, and if the calibration of the rigid component is still holding properly, $$\begin{bmatrix} \lambda^i u^i \\ \lambda^i v^i \\ \lambda^i \end{bmatrix} = P_{\theta^i} * \begin{bmatrix} x_f \\ y_f \\ z_f \\ 1 \end{bmatrix}$$

is obtained for $1 \leq i \leq N$;

wherein in this equation, $(u^i, v^i)$, $P_{\theta^i}$ are known but $(x_f, y_f, z_f)$ and $\lambda^i$ are unknown.

Next, a known three-dimensional point $(x_f^{known}, y_f^{known}, z_f^{known})$ is chosen, and its expected two-dimensional projection is computed for the gantry angles $\theta^1, \ldots, \theta^N$ under the assumption that the calibration of the rigid component is still valid; and as a result $$\begin{bmatrix} w^i u^{i\,known} \\ w^i v^{i\,known} \\ w^{i\,known} \end{bmatrix} = P_{\theta^i} * \begin{bmatrix} x_f^{known} \\ y_f^{known} \\ z_f^{known} \\ 1 \end{bmatrix}$$

is obtained, for $1 \leq i \leq N$, where in this equation $(u^{i\,known}, v^{i\,known})$, are computed from known values of $(x_f^{known}, y_f^{known}, z_f^{known})$ and $P_{\theta^i}$; and Corresponding equations are subtracted to obtain:

$$\begin{bmatrix} w^i u^{i\,known} - \lambda^i u^i \\ w^i v^{i\,known} - \lambda^i v^i \\ w^{i\,known} - \lambda^i \end{bmatrix} = P_{\theta^i} * \begin{bmatrix} x_f^{known} - x_f \\ y_f^{known} - y_f \\ z_f^{known} - z_f \\ 1 - 1 \end{bmatrix} = P_{\theta^i} * \begin{bmatrix} k_x \\ k_y \\ k_z \\ 0 \end{bmatrix},$$

where $(k_x, k_y, k_z)$ is the unknown constant three-dimensional vector from the unknown bead location $(x_f, y_f, z_f)$ to the known three dimensional point $(x_f^{known}, y_f^{known}, z_f^{known})$.

For a given gantry angle $\theta^i$, there are three equations and four unknowns, $\lambda^i$, $k_x$, $k_y$, $k_z$. However, the three-dimensional unknown vector $(k_x, k_y, k_z)$ is common to all gantry angles. Therefore, under the assumption that the calibration of the rigid component is still holding properly, six equations from two gantry angles $(\theta^p, \theta^q)$ can be used to find five unknowns value $(\lambda^p, \lambda^q, k_x, k_y, k_z)$.

Thus, the assumption of whether the second sub matrix (i.e., the calibration of rigid components) is sufficiently valid can now be checked. From the projections corresponding to gantry angles $\theta^1, \ldots, \theta^N$, many pairs of projections, preferably orthogonal to one another, are obtained. $(k_x, k_y, k_z)$ is computed from each such pair. In other words, the unknown location $(x_f, y_f, z_f)$ of each bead can be computed from each such projection pair assuming that the second sub-matrix is still valid. If sufficient agreements in the computed values of the unknown location of the beads are found, it can be concluded that the second sub-matrix is valid.

It should be understood that the embodiments presented above are examples rather than limitations. Those in the art can modify and vary the embodiments without departing from their spirit and scope.

What is claimed is:

1. A method for calibrating an imaging system including an imaging source and an image detector, the method comprising:

determining a first sub-matrix of a projection matrix, the projection matrix describing a geometrical relationship between points of a three-dimensional (3D) coordinate system of the imaging system and points of a two-dimensional (2D) coordinate system of the image detector;

determining a second sub-matrix of the projection matrix, each of the first sub-matrix and the second sub-matrix including a decomposition of the projection matrix; and converting a first point of the two-dimensional coordinate system of the imaging system to a first point of the three-dimensional coordinate system of the imaging system based on the first sub-matrix and the second sub-matrix.

2. The method of claim 1, further comprising:
determining an updated first sub-matrix of an updated projection matrix by calibrating the first sub-matrix according to a first calibration schedule, the updated projection matrix describing a second geometrical relationship between points of the 3D coordinate system and points of the 2D coordinate system, each of the updated first sub-matrix and the second sub-matrix including a decomposition of the updated projection matrix; and
converting a second point of the 2D coordinate system to a second point of the 3D coordinate system based on the updated first sub-matrix and the second sub-matrix.

3. The method of claim 2, further comprising:
determining an updated second sub-matrix of a second updated projection matrix by calibrating the second sub-matrix according to a second calibration schedule, the second updated projection describing a third geometrical relationship between points of the 3D coordinate system and points of the 2D coordinate system, each of the updated first sub-matrix and the updated second sub-matrix including a decomposition of the second updated projection matrix; and
converting a third point of the 2D coordinate system to a third point of the 3D coordinate system based on the updated first sub-matrix and the updated second sub-matrix.

4. The method of claim 3, wherein determining the updated second sub-matrix comprising:
acquiring a plurality of projection images of a plurality of fiducials at different gantry angles;
generating a 3D image of the plurality of fiducials based on the plurality of projection images;
determining a first value of a first parameter related to the plurality of fiducials based on the three-dimensional image;
determining whether a difference between the first value of the first parameter related to the plurality of fiducials and a second value of the first parameter of the plurality of fiducials is greater than a threshold; and
in response to the determination that a difference between the first value of the first parameter related to the plurality of fiducials and a second value of the first parameter of the plurality of fiducials is greater than the threshold, determining the updated second sub-matrix of the second updated projection matrix.

5. The method of claim 4, wherein the first parameter comprises a dimension or blur related to the plurality of fiducials.

6. The method of claim 3, wherein determining the updated second sub-matrix comprising:
acquiring a plurality of projections of a fiducial at a plurality of gantry angles;
determining a plurality of values related to a location of the fiducial based on the plurality of gantry angles;
determining whether a condition is satisfied among the plurality of values; and
in response to the determination that the condition is satisfied, determining the updated second sub-matrix of the second updated projection matrix.

7. The method of claim 6, wherein each of the plurality of values related to the location is determined with respect to a reference point.

8. The method of claim 7, wherein each of the plurality of values related to the location is determined based on at least two of the plurality of gantry angles.

9. The method of claim 1, wherein determining the first sub-matrix comprises:
determining an in-plane rotation of the image detector; and
determining a point of the 2D coordinate system which is intercepted by a beam axis of the imaging source.

10. The method of claim 9, wherein determining the first sub-matrix comprises:
acquiring a projection image of a predefined collimator leaf pattern;
determining one or more differences between the projection image of the predefined collimator leaf pattern and an expected projection image of the predefined collimator leaf pattern; and
determining the in-plane rotation of the image detector and the point of the 2D coordinate system based on the one or more differences.

11. An imaging system comprising:
an imaging source configured to emit radiation;
an image detector configured to receive the radiation and to generate an image based on the received radiation; and
a processing unit configured to execute program codes stored in a non-transitory computer-readable medium to cause the image system to:
determine a first sub-matrix of a projection matrix, the projection matrix describing a geometrical relationship between points of a three-dimensional (3D) coordinate system of the imaging system and points of a two-dimensional (2D) coordinate system of the image detector;
determine a second sub-matrix of the projection matrix, each of the first sub-matrix and the second sub-matrix including a decomposition of the projection matrix; and
convert a first point of the two-dimensional coordinate system of the imaging system to a first point of the three-dimensional coordinate system of the imaging system based on the first sub-matrix and the second sub-matrix.

12. The imaging system of claim 11, wherein the processing unit is further configured to execute the program codes to cause the imaging system to:
determine an updated first sub-matrix of an updated projection matrix by calibrating the first sub-matrix according to a first calibration schedule, the updated projection matrix describing a second geometrical relationship between points of the 3D coordinate system and points of the 2D coordinate system, each of the updated first sub-matrix and the second sub-matrix including a decomposition of the updated projection matrix; and
convert a second point of the 2D coordinate system to a second point of the 3D coordinate system based on the updated first sub-matrix and the second sub-matrix.

13. The imaging system of claim 12, wherein the processing unit is further configured to execute the program codes to cause the imaging system to:
determine an updated second sub-matrix of a second updated projection matrix by calibrating the second sub-matrix according to a second calibration schedule, the second updated projection describing a third geometrical relationship between points of the 3D coordinate system and points of the 2D coordinate system, each of the updated first sub-matrix and the updated second sub-matrix including a decomposition of the second updated projection matrix; and convert a third point of the 2D coordinate system to a third point of the 3D coordinate system based on the updated first sub-matrix and the updated second sub-matrix.

14. The imaging system of claim 13, wherein to determine the updated second sub-matrix, the processing unit is further configured to execute the program codes to cause the imaging system to:

acquire a plurality of projection images of a plurality of fiducials at different gantry angles;

generate a 3D image of the plurality of fiducials based on the plurality of projection images;

determine a first value of a first parameter related to the plurality of fiducials based on the three-dimensional image;

determine whether a difference between the first value of the first parameter related to the plurality of fiducials and a second value of the first parameter of the plurality of fiducials is greater than a threshold; and in response to the determination that a difference between the first value of the first parameter related to the plurality of fiducials and a second value of the first parameter of the plurality of fiducials is greater than the threshold, determine the updated second sub-matrix of the second updated projection matrix.

15. The imaging system of claim 14, wherein the first parameter comprises a dimension or blur related to the plurality of fiducials.

16. The imaging system of claim 13, wherein to determine the updated second sub-matrix, the processing unit is further configured to execute the program codes to cause the imaging system to:

acquire a plurality of projections of a fiducial at a plurality of gantry angles;

determine a plurality of values related to a location of the fiducial based on the plurality of gantry angles;

determine whether a condition is satisfied among the plurality of values; and in response to the determination that the condition is satisfied, determine the updated second sub-matrix of the second updated projection matrix.

17. The imaging system of claim 16, wherein each of the plurality of values related to the location is determined with respect to a reference point.

18. The imaging system of claim 17, wherein each of the plurality of values related to the location is determined based on at least two of the plurality of gantry angles.

19. The imaging system of claim 11, wherein to determine the first sub-matrix comprises, the processing unit is further configured to execute the program codes to cause the imaging system to:

determine an in-plane rotation of the image detector; and determine a point of the 2D coordinate system that is intercepted by a beam axis of the imaging source.

20. A non-transitory computer readable medium storing instructions, the instructions, when executed by a computing device, causing the computing device to implement a method, the method comprising:

determining a first sub-matrix of a projection matrix, the projection matrix describing a geometrical relationship between points of a three-dimensional (3D) coordinate system of the imaging system and points of a two-dimensional (2D) coordinate system of the image detector;

determining a second sub-matrix of the projection matrix, each of the first sub-matrix and the second sub-matrix including a decomposition of the projection matrix; and converting a first point of the two-dimensional coordinate system of the imaging system to a first point of the three-dimensional coordinate system of the imaging system based on the first sub-matrix and the second sub-matrix.

* * * * *